United States Patent [19]

Bachovchin et al.

[11] Patent Number: 4,935,493

[45] Date of Patent: Jun. 19, 1990

[54] PROTEASE INHIBITORS

[75] Inventors: William W. Bachovchin, Melrose; Andrew G. Plaut, Lexington, both of Mass.; Charles A. Kettner, Wilmington, Del.

[73] Assignees: E. I. Du Pont de Nemours and Company, Wilmington, Del.; New England Medical Center Hospitals, Inc., Boston; Tufts University, Medford, both of Mass.

[21] Appl. No.: 105,768

[22] Filed: Oct. 6, 1987

[51] Int. Cl.$^5$ .................... A61K 37/02; C07K 5/08; C07K 5/10
[52] U.S. Cl. ..................... 530/331; 530/330
[58] Field of Search .............. 514/2, 18, 19; 530/330, 530/331

[56] References Cited

U.S. PATENT DOCUMENTS

| | | | |
|---|---|---|---|
| 4,318,904 | 3/1982 | Shaw et al. | 424/177 |
| 4,499,082 | 2/1985 | Shenvi et al. | 514/2 |
| 4,582,821 | 4/1986 | Kettner et al. | 514/18 |
| 4,636,492 | 1/1987 | Kettner et al. | 514/18 |
| 4,644,055 | 2/1987 | Kettner et al. | 530/330 |
| 4,652,552 | 3/1987 | Kettner et al. | 514/18 |

OTHER PUBLICATIONS

R. Baugh et al., Proteinases and Tumor Invasion 157–179, 165 (ed. Strauli et al., 1980).
Cordes et al., Transition States of Biochemical Processes 429–465 (ed. Gandour et al., 1978).
Matteson et al., 1984, Organometallics 3:1284.
Thompson, 1973, Biochemistry 12:47.
Thompson, Methods in Enzymology 46:220–225.
Yoshimoto et al., 1985, J. Biochem 98:975.
Report of the National Heart Lung and Blood Institute Workshop on Elastase Inhibitors for Treatment of Emphysema held in Rockville, Md. (Jun. 10–11, 1985).

*Primary Examiner*—Lester L. Lee
*Attorney, Agent, or Firm*—Fish & Richardson

[57] ABSTRACT

A compound having the structure

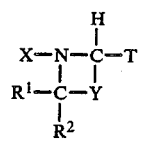

where T is of the formula

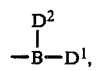

where each $D^1$ and $D^2$, independently, is a hydroxyl group of a group which is capable of being hydrolysed to a hydroxyl group in aqueous solution at physiological pH; a group of the formula

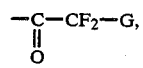

where G is either H, F or an alkyl group containing 1 to about 20 carbon atoms and optional heteroatoms which can be N, S, or O; or a phosphonate group of the formula

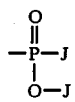

where J is O-alkyl, N-alkyl, or alkyl, each comprising about 1–20 carbon atoms and, optionally, heteroatoms which can be N, S, or O; T being able to form a complex with the catalytic site of an enzyme, X is a group having at least one amino acid, (Abstract continued on next page.)

-continued
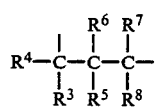
and each $R^1$, $R^2$, $R^3$, $R^4$, $R^5$, $R^6$, $R^7$, and $R^8$ is separately a group which does not interfere significantly (i.e., does not lower than Ki of the compound to less than $10^{-7}$M) with site-specific recognition of the compound by the enzyme, and allows a complex to be formed with the enzyme.
12 Claims, 2 Drawing Sheets

Prolyl Boronate

Prolyl Trifluoro alkyl ketone

Prolyl phosphonate 4-bromo-1-chlorobutyl boronate pinacol 4-bromo-1 [(bistrimethylsilyl) amino] butyl bornonate pinacol 1-trimethylsilyl-boroProline pinacol     boroProline-pinacol-HCl Boc-Ala-Pro-boroPro-pinacol

PROTEASE INHIBITORS

BACKGROUND OF THE INVENTION

This invention relates to protease inhibitors, and particularly to transition state analogs.

Transition state analogs, compounds which are thought to resemble the substrates of enzymes, are thought to bind more tightly to the enzymes than the substrates themselves. Transition state analogs form complexes with enzymes at their catalytic sites.

Baugh et al. (Proteinases and Tumor Invasion ed. Strauli et al., Raven Press, N.Y., 1980, p. 165) state that transition state analogs containing boronic acid moieties or aldehydes form tetrahedral adducts with serine proteases and are thus good inhibitors of these enzymes. Further, they state that some peptide aldehydes have been synthetically prepared, that most are of microbial origin, and that "it would appear that changing the R-group [of synthetic peptides] to satisfy the specific requirements of a given protease should result in both potent and specific inhibitors." They also state that transition state analogs containing cyclic ester moieties have been used to inhibit chymotrypsin and that "variations thereof may become useful as inhibitors of cathepsin G."

Yoshimoto et al. (J. Biochem .98: 975, 1985) describe prolyl endopeptidase inhibitors containing a protinal moiety. These inhibitors appear to act non-competitively.

Shenvi et al., U.S. Pat. No. 4,499,082, describe peptides having an α-amino boronic acid residue. These peptides are reversible inhibitors of elastase. They have the structureal formula

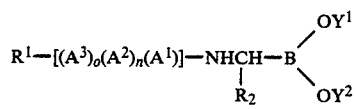

where $R_2$ is an alkyl group of one to six carbons which may have an aromatic substituent or an in-chain bivalent group.

SUMMARY OF THE INVENTION

In a first aspect, the invention features compounds having the structure

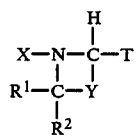 (1)

and salts thereof, where T is a boronate group of the formula

where each $D^1$ and $D^2$, independently, is a hydroxyl group or a group which is capable of being hydrolyzed to a hydroxyl group in aqueous solution at physiological pH; or T is a group of the formula

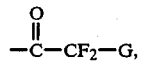 (2)

where G is either H, F or an alkyl group containing 1 to about 20 carbon atoms and optional heteroatoms which can be N, S, or O; or T is a phosphonate group of the formula

 (3)

where each J, independently, is O-alkyl, N-alkyl, or alkyl (each containing about 1–20 carbon atoms) and, optionally, heteroatoms which can be N, S, or O; where T is a group able to form a complex with the catalytic site of an enzyme; X includes one or more amino acids,

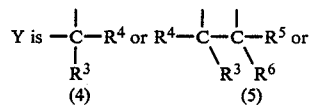

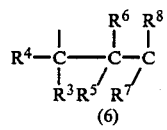

and each $R^1$, $R^2$, $R^3$, $R^4$, $R^5$, $R^6$, $R^7$, and $R^8$, independently, is a group which does not interfere significantly (i.e., does not raise the Ki of the compound to greater than $10^{-5}$M) with site-specific recognition of the compound by the enzyme, while permitting a complex to be formed between the compound and the enzyme.

In preferred embodiments, T is a boronate group, each $D^1$ and $D^2$, independently, is OH or F or $D^1$ and $D^2$ together form a ring containing 1 to about 20 carbon atoms, and optionally heteroatoms which can be N, S, or O; each $R^{1-8}$ is H; X mimics the substrate recognized by the enzyme, for example X is pro-, thr-pro-, ala-pro-, ala-ala-pro, ser-thr-pro-, pro-ser-, pro-thr- or ser-pro- (pro=proline, thr=threonine, and ser=serine); X contains both an amino acid and a blocking group, such as an acetyl group; the enzymes inhibited by the compounds of the invention are post prolyl cleaving enzymes, most preferably serine proteases, even more preferably IgA1 proteases; and the analog has a binding constant of at least $10^{-7}$M, most preferably $10^{-10}$M.

In a second aspect, the invention features a compound, which is useful as an intermediate in the synthesis of compounds of Formula (1), having the formula

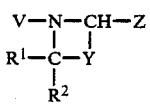 (7)

where V is (CH₃)₃Si— or H—,
Y is

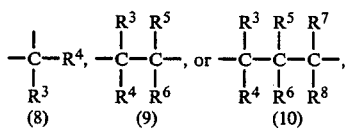

each $R^1$, $R^2$, $R^3$, $R^4$, $R^5$, $R^6$, $R^7$, and $R^8$ is independently H, or $C_1$-$C_{10}$ alkyl or aryl, and

where $D^1$ and $D^2$ are as defined above.

The invention also features a method for producing the above compounds. The method includes the steps of reacting a compound of the formula

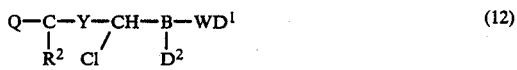

where Q is Cl or Br, and $R^2$, Y, Z, and $D^1$ and $D^2$ are as defined above, with a compound of the formula

in an inert solvent at a temperature between $-78°$ C. and $25°$ C., and heating the reaction mixture to at least $80°$ C.

In preferred embodiments the reacting step is performed in the absence of an inert solvent.

The compounds of the invention are peptide derivatives (or intermediates in their formation) which are potent inhibitors of proteolyic enzymes (especially those produced by pathogens) which are post-prolyl cleaving enzymes, e.g., the proteases able to act on IgA1 proteins. The compounds generally have a proline, proline analog, a 2-azetidinecarboxylic acid, or pipecolic acid linked to a group, for example a boronate group, which mimics the transition state of an enzyme substrate, and to a peptide moiety which preferably mimics the site of the substrate acted upon by the enzyme of interest. It is proposed that the peptide moiety is recognized as a substrate by the enzyme to be inhibited, and it then enters an active site, catalytic site, or transition state binding site of the enzyme, and the transition state-mimicing group of the compound of the invention binds strongly at this site. This binding advantageously prevents the enzyme from acting upon its natural substrate. The high affinity of these compounds make them effective at concentrations as low as $10^{-7}$M, or even $10^{-10}$M.

Thus, the present invention also provides compositions including one or more compounds of formula 1 above, and methods of using such compounds or compositions in the inhibition of post prolyl cleaving enzymes.

Other features and advantages of the invention will be apparent from the following description of preferred embodiments thereof, and from the claims.

DESCRIPTION OF THE PREFERRED EMBODIMENTS

The Figures will first briefly be described.

Drawing

STRUCTURE

The compounds of the invention have the general structure recited in the Summary of the Invention above. Examples of preferred structures are those referred to as preferred embodiments above.

The structure of the compounds is such that at least a portion of the amino acid sequence near the cleavage site of a post-prolyl cleaving enzyme substrate is duplicated, or nearly duplicated. This duplication is in part responsible for the ability of the compounds to inhibit the enzyme, by a mechanism thought to involve competitive inhibition between the compound and the actual enzyme substrate.

The choice of amino acid sequence affects the inhibitory activity of the compound, and its specificity. As a first step in determining a suitable sequence, the amino acid sequence of the substrate is determined near its cleavage site. In some cases, such as for serine proteases, a suitable inhibitor sequence is the amino acid sequence N-terminal to (i.e., to the left of) the proline cleavage point, and includes that proline. Peptide fragments can be synthesized and then tested to determine their efficacy as inhibitors, using standard techniques. Specificity is determined in a similar fashion, by testing the inhibitory effect of a particular compound on a variety of enzyme activities. The compounds preferably inhibit the activity of enzymes detrimental to an animal or human patient, and preferably do not inhibit necessary enzymes.

The compounds of the invention can be designed so that they are resistant to attack by agents which might otherwise cause their catabolic degradation by cleavage of one or more peptide bonds in the peptides. For example, an N-terminal blocking group, such as acetyl, can increase the half-life of the compounds in vivo, and thus improves inhibition.

The structure of such blocking groups can vary widely. In one blocking reaction, a hydrogen atom of the amino terminal amino group is replaced, generally in a dehydration reaction. Thus, blocking groups such as

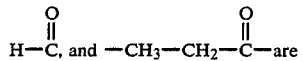

are readily added to a peptide chain. Others include

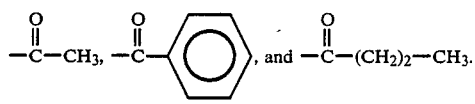

Such N-terminal blocking groups may be employed not only to protect amino-terminal groups, but also may protect-side chain amino group of amino acids which make up X, such as where X includes Lys or Arg. Similarly, amino acid residues having acidic or hydroxy side chains can be protected in the form of t-butyl, benzyl, or other suitable esters or ethers. Short length of the compounds of the invention (2–7, preferably 3 or 4 amino acids) is advantageous because it provides stability and increased half life.

Figure 1:
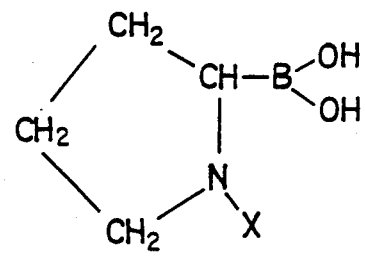
FIG. 1 shows the general formula of three preferred compounds.
Figure 1:
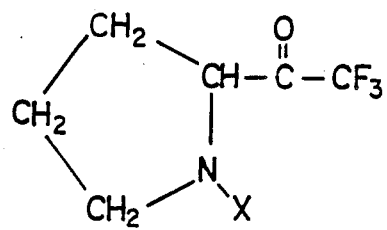
Figure 1:
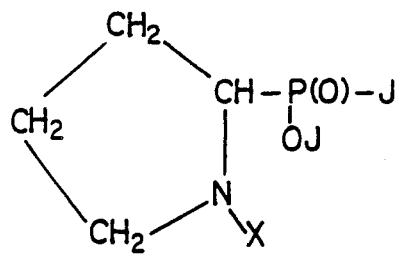

The compounds also include a group (T) which causes the compound to complex with an enzyme, not only in a competitive fashion, but in a chemically reactive manner to form a strong bond between the compound and the enzyme. This group thus acts to bind the compound to the enzyme, and increases the inhibitory binding constant (Ki) of the compound. Examples of such groups include boronates, fluoroalkyl ketones and substituted phosphonates (of the formulae given in the Summary above, examples of which are shown in FIG. 1). These groups are covalently bonded to the prolyl residue of the compound, as in the above formula.

The proline or proline analog, represented by

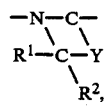 (14)

above, is chosen so that it mimics the structure of proline recognized by the active site of the enzyme to be inhibited. It can be modified by providing $R^{1-2}$ groups which do not interfere significantly with this recognition and thus do not significantly affect the Ki of a compound. Thus, one or more hydroxyl groups can be substituted to form hydroxy-proline, and methyl or sugar moieties may be linked to these groups. One skilled in the art will recognize that these groups are not critical in this invention and that a large choice of substituents are acceptable for R.

Examples of compounds having utility as serine protease inhibitors include compounds having a peptide chain similar to the subtrate of IgA1 and IgA2 proteases. Plaut 1983 *Ann Rev. Microbiol.* 37, 603–622). These enzymes hydrolyze specific peptide bonds of IGA, the immunoglobulin that provides antibody defense of mucosal surfaces, resulting in a nonfunctional immunoglobulin and impairment of the host defense system. This is expected to be a strong contributing factor to pathogenesis of organisms such as *Streptococcus sanquis, S. pneumoniae, Neisseria gonorrhoae, N. meningitidis,* and *Haemophilus influenzae.*

IgA1 proteases recognize the cleavage site Ser-Thr-Pro-Pro-X (where X is any amino acid), hydrolyzing between Pro and X (i.e., they are post prolyl cleaving enzymes). Accordingly, Ser-Thr-Pro-Pro-T is a suitable compound of the invention for inhibiting IGA1 proteases. The Ser or Thr in this compound can be readily substituted with any of the 20 naturally occurring amino acids, most preferably those having non-bulky side groups, such as Ala and Gly. It is also possible to substitute non-naturally occurring amino acids, such as 2-azetidinecarboxylic acid or pipecolic acid (which have six-membered, and four-membered ring structures respectively) for either of the Pro residues. Those skilled in the art will recognize that there are other such changes which can be made without significantly affecting the inhibitory character of these compounds.

In the case of IgA2, the cleavage site is Pro-Thr-Pro-X, with hydrolysis occurring between Pro and X. Thus, a preferred compound of the invention for inhibiting IGA2 proteases has the formula Pro-Thr-Pro-T. Thr can be substituted by any of the naturally occurring amino acids, especially ones having non-bulky side groups, such as Ala, Gly, or Ser.

Other examples of enzymes which can be inhibited according to the invention include other post prolyl cleaving enzymes, such as IgA enzymes, enkephalin degrading enzymes, vasopressin degrading enzymes, and oxytosin degrading enzymes. Further, the serine protease, dipeptidyl peptidase Type IV, on T-lymphocytes (Andrews et al., *Clin. Lab. Haemato.* 7: 359–368, 1985), which plays a role in regulation of the immune response, can be inhibited by suitable such compounds. These inhibitors may be useful in treatment of Aids. Walters et al., *Molecular and Cellular Biochemistry* 30: 111–127, 1980 describe other such enzymes, and are hereby incorporated by reference.

Synthesis

Synthesis of boroProline

Figure 2:
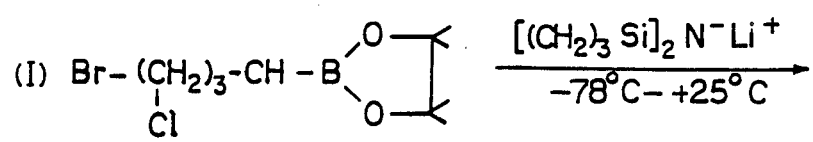
FIG. 2 is a diagrammatic representation of the synthesis of a boroProline compound.
Figure 2:
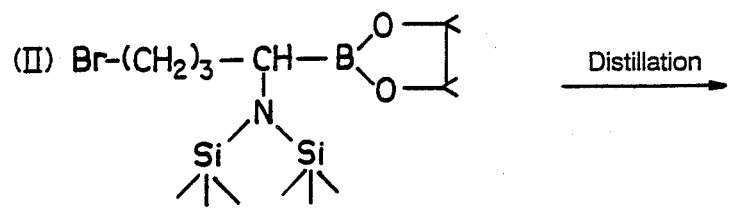
Figure 2:
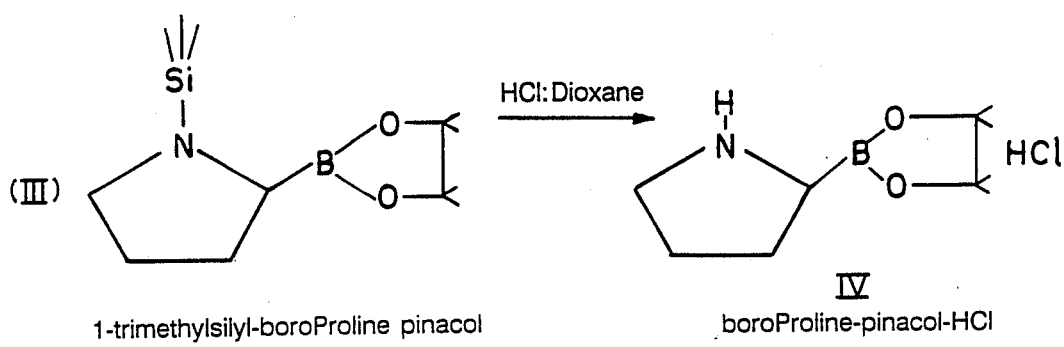
Figure 2:
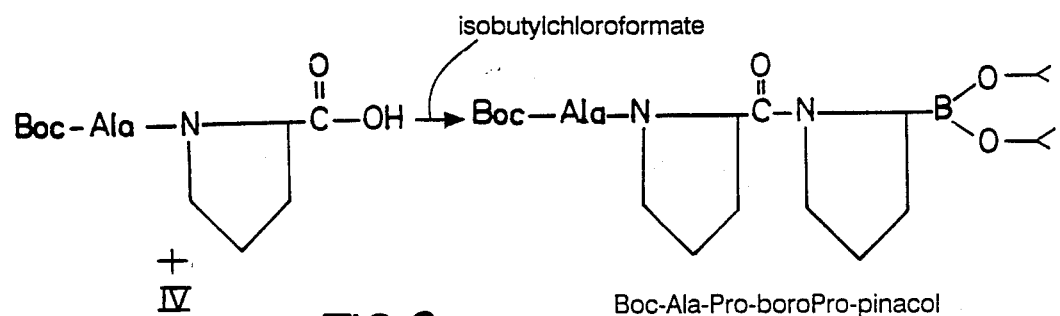

Referring to FIG. 2, the starting compound I is prepared essentially by the procedure of Matteson et al., 3 *Organometallics* 1284, 1984, except that a pinacol ester is substituted for the pinanediol ester. Similar compounds such as boropipecolic acid and 2-azetodine boronic acid can be prepared by making the appropriate selection of starting material to yield the pentyl and propyl analogs of compound I. Further, Cl can be substituted for Br in the formula, and other diol protecting groups can be substituted for pinacol in the formula, e.g., 2,3-butanediol and alpha-pinanediol.

Compound II is prepared by reacting compound I with $[(CH_3)O_3Si]_2N^-Li^+$. In this reaction hexamethyldisilazane is dissolved in tetrahydrofuran and an equivalent of n-butyllithium added at $-78°$ C. After warming to room temperature (20° C.) and cooling to $-78°$ C. an equivalent of compound I is added in tetrahydrofuran. The mixture is allowed to slowly come to room temperature and to stir overnight. The alpha-bis[trimethylsilane]-protected amine is isolated by evaporating solvent and adding hexane under anhydrous conditions. Insoluble residue is removed by filtration under a nitrogen blanket, yielding a hexane solution of compound 2.

Compound III, the N-trimethysilyl protected form of boroProline is obtained by the thermal cyclization of compound II during the distillation process in which compound II is heated to 100°–150° C. and distillate is collected which boils 66°–62° C. at 0.06–0.10 mm pressure.

Compound IV, boroProline-pinacol hydrogen chloride, is obtained by treatment of compound III with HCl:dioxane. Excess HCl and by-products are removed by trituration with ether. The final product is obtained in a high degree of purity by recrystallization from ethyl acetate. H-boroProline as the hydrochloride salt is preferred, but other salts forms such as the hydrobromide and trifluoroacetate can readily be obtained by substitution of the appropriate acid for HCl.

The boroProline esters can also be obtained by treatment of the reaction mixture obtained in the preparation of compound II with anhydrous acid to yield 1-amino-4-bromobutyl boronate pinacol as a salt. Cyclization occurs after neutralizing the salt with base and heating the reaction.

Synthesis of boroProline Peptides

General methods of coupling of N-protected peptides and amino acids with suitable side-chain protecting groups to H-boroProline-pinacol are applicable. When needed, side-chain protecting and N-terminal protecting groups can be removed by treatment with anhydrous HCl, HBr, trifluoroacetic acid, or by catalytic hydrogenation. These procedures are known to those skilled in the art of peptide synthesis. One exception is that in the preparation of a compound with the Pro-Thr-boroPro sequence. Removal of acid labile protecting groups from threonine hydroxyl group results in a complex mixture of products. Thus, the use of hydrogenolytic protecting groups for threonyl residue is preferred.

The mixed anhydride procedure of Anderson et al., *J. Am. Chem. Soc.*, 89:5012 (1984) is preferred for peptide coupling. The mixed anhydride of an N-protected amino acid or a peptide varying in length from a dipeptide to tetrapeptide is prepared by dissolving the peptide in tetrahydrofuran and adding one equivalent of N-methylmorpholine. The solution is cooled to −20° C. and an equivalent of isobutyl chloroformate is added. After 5 minutes, this mixture and one equivalent of triethylamine (or other sterically hindered base) are added to a solution of H-boroPro-pinacol dissolved in either cold chloroform or tetrahydrofuran.

The reaction mixture is routinely stirred for one hour at −20° C. and 1–2 hours at room temperature (20° C.). Solvent is removed by evaporation, and the residue is dissolved in ethyl acetate. The organic solution is washed with 0.20N hydrochloric acid, 5% aqueous sodium bicarbonate, and saturated aqueous sodium chloride. The organic phase is dried over anhydrous sodium sulfate, filtered, and evaporated. Products are purified by either silica gel chromatography or gel permeation chromatography using Sephadex ™ LH-20 and methanol as a solvent.

Previous studies have shown that the pinacol protecting group can be removed in situ by preincubation in phosphate buffer prior to running biological experiments; Kettner et al., *J. Biol. Chem.* 259: 15106–15114 (1984). Several other methods are also applicable for removing pinacol groups from peptides including boro-Proline and characterizing the final product. First, the peptide can be treated with diethanolamine to yield the corresponding diethanolamine boronic acid ester, which can be readily hydrolyzed by treatment with aqueous acid or a sulfonic acid substituted polystyrene resin as described in Kettner et al., Id. Both pinacol and pinanediol protecting groups can be removed by treating with $BCl_3$ in methylene chloride as described by Kinder et al., *J. Med. Chem.*, 28: 1917. Finally, the free boronic acid can be converted to the difluoroboron derivative ($-BF_2$) by treatment with aqueous HF as described by Kinder et al., Id.

Similarly, different ester groups can be introduced by reacting the free boronic acid with various di-hydroxy compounds (for example, those containing heteroatoms such as S or N) in an inert solvent.

The following abbreviations are used in the examples below. THF - tetrahydrofuran; H-Pro-OBzl - the benzyl ester of proline; H-Thr (OBzl)-OH - the benzyl ether derivative of threonine; Boc - the tertiary butyloxycarbonyl group; FABMS - fast atom bombardment mass spectometry.

All natural amino acids are in the L-configuration. H-boroProline is in the D,L-configuration.

EXAMPLE 1

Preparation of boroProline-pinacol
(H-boroPro-pinacol)

The intermediate, 4-Bromo-1-chlorobutyl boronate pinacol, was prepared by the method in Matteson et al., *Organometallics*, (3): 1284–1288 (1984), except that conditions were modified for large scale preparations and the pinacol was substitued for the pinanedoil protecting group.

3-bromopropyl boronate pinacol was prepared by hydrogenboronation of allyl bromide (173 ml, 2.00 moles) with catechol borane (240 ml, 2.00 moles). Catechol borane was added to allyl bromide and the reaction heated for 4 hours at 100° C. under a nitrogen atmosphere. The product, 3-bromopropyl boronate catechol (bp 95°–102° C., 0.25 mm), was isolated in a yield of 49% by distillation. The catechol ester (124 g, 0.52 moles) was transesterified with pinacol (61.5 g, 0.52 moles) by mixing the component in 50 ml of THF and allowing them to stir for 0.5 hours at 0° C. and 0.5 hours at room temperature. Solvent was removed by evaporation and 250 ml of hexane added. Catechol was removed as a crystalline solid. Quantitative removal was achieved by successive dilution to 500 ml and to 1000 ml with hexane and removing crystals at each dilution. Hexane was evaporated and the product distilled to yield 177 g (bp 60°–64° C., 0.35 mm).

4-Bromo-1-chlorobutyl boronate pinacol was prepared by homologation of the corresponding propyl boronate. Methylene chloride (50.54 ml, 0.713 moles) was dissolved in 500 ml of THF, 1.54N n-butyllithium in hexane (480 ml, 0.780 moles) was slowly added at −100° C. 3-Bromopropyl boronate pinacol (178 g, 0.713 moles) was dissolved in 500 ml of THG, cooled to the freezing point of the solution, and added to the reaction mixture. Zinc chloride (54.4 g, 0.392 moles) was dissolved in 250 ml of THG, cooled to 0° C., and added to the reaction mixture in several portions. The reaction was allowed to slowly warm to room temperature and to stir overnight. Solvent was evaporated and the residue dissolved in hexane (1 liter) and washed with water (1 liter). Insoluble material was discarded. After drying over anhydrous magnesium sulfate and filtering, solvent was evaporated. The product was distilled to yield 147 g (bp 110°–112° C. 0.200 mm).

N-Trimethylsilyl-boroProline pinacol was prepared first by dissolving hexamethyldisilizane (20.0 g, 80.0 mmoles) in 30 ml of THF, cooling the solution to −78° C. and adding 1.62N n-butyllithium in hexane (49.4 ml, 80.0 mmoles). The solution was allowed to slowly warm to room temperature. It was recooled to −78° C. and 4-bromo-1-chlorobutyl boronate pinacol (23.9 g, 80.0 mmoles) added in 20 ml of THF. The mixture was allowed to slowly warm to room temperature and to stir overnight. Solvent was removed by evaporation and dry hexane (400 ml) added to yield a precipitant which was removed by filtration under an nitrogen atmosphere. The filtrate was evaporated and the residue distilled, yielding 19.4 g of the desired product (bp 60°–62° C., 0.1–0.06 mm).

H-boroProline-pinacol.HCl was prepared by cooling N-trimethylsilyl-boroProline-pinacol (16.0 g, 61.7 mmoles) to −78° C. and adding 4N HCL:dioxane 46 ml, 185 mmoles). The mixture was stirred 30 minutes at −78° C. and 1 hour at room temperature. Solvent was evaporated and the residue triturated with ether to yield a solid. The crude product was dissolved in chloroform and insoluble material removed by filtration. The solution was evaporated and the product crystallized from ethyl acetate to yield 11.1 g of the desired product (mp 156.5°–157° C.).

EXAMPLE 2

Preparation of Boc-Ala-Pro-boroPro-pinacol

Boc-Ala-Pro-boroPro-pinacol was prepared by coupling Boc-Ala-Pro-OH to H-boroPro-pinacol. First, the dipeptide, Boc-Ala-Pro-OBzl, was prepared by the mixed anhydride procedure. Boc-Ala-OH (10 g, 52.8 mmoles) was reacted with N-methylmorpholine (5.8 ml, 52.8 mmoles) and isobutyl chloroformate (6.8 ml, 52.8 mmole) for 5 minutes in 50 ml of THF at −20°. The reaction mixture and additional N-methylmorpholine (5.8 ml) were added to H-Pro-OBzl.HCL (12.8 g, 52.8 mmoles) dissolved in 50 ml of cold chloroform. After the mixture was stirred for 1 hour at −20° C. and 2 hours at room temperature, it was filtered and the filtrate evaporated. The residue was dissolved in ethyl acetate and washed sequentially with 0.2N hydrochloric acid, 5% aqueous $NaCO_3$, and saturated aqueous NaCl. The organic phase was dried over anhydrous $Na_2SO_4$, filtered, and evaporated to yield Boc-Ala-Pro-OBzl as an oil (14.1 g). The benzyl ester protecting group was removed by dissolving Boc-Ala-Pro-OBzl (35 g, 92.8 mmoles) in 200 ml of methanol and hydrogenating for 1 hour in the presence of 0.5 g of 10% Pd/C. The catalyst was removed by filtration and the solvent evaporated. The residue was crystallized from ethyl acetate to yield 16.1 g of Boc-Ala-Pro-OH (mp 153.5°–154.5° C.).

Boc-Ala-Pro-OH (1.26 g, 4.28 mmoles) was coupled to H-boroPro-pinacol by the general procedure described for the preparation of Boc-Ala-Pro-OBzl. Boc-Ala-Pro-OH (1.26 g, 4.28 mmoles) was dissolved in 10 ml of THF and cooled to −20° C.; N-methylmorpholine (0.47 ml, 4.28 mmoles) and isobutyl chloroformate (0.557 ml, 4.28 mmoles) were added. After stirring for 5 minutes, 10 ml of cold THF and triethylamine (0.597 ml, 4.28 mmoles) were added and the mixture added to a cold solution of H-boroPro-pinacol.HCl (1.0 g, 4.28 mmoles) in 5 ml chloroform. After dissolving the reaction product in ethyl acetate and washing with aqeous HCl, $NaHCO_3$, and saturated aqueous NaCl, 0.39 g of material were obtained. It was further purified by chromatography on a 2.5×50 cm column of Sephadex LH-20 in methanol to yield 0.25 g.

EXAMPLE 3

Preparation of H-Ala-Pro-boroPro-pinacol.HCL

Boc-Ala-Pro-boroPro-pinacol (0 58 g, 1.25 mmoles) was allowed to react with 2.5 mol of 4N HCl:dioxane for 30 minutes at room temperature. Ether (50 ml) was added to yield 0.22 g of amorphous white solid.

EXAMPLE 4

Preparation of Ac-Ala-Pro-boroPro-pinacol

H-Ala-Pro-boroPro-pinacol.HCL (0.22 g, 0.55 mmoles) was dissolved in 3 ml of THF and cooled to 0° C. Acetic anhydride (0.078 ml, 0.825 mmoles) and triethylamine (0.115 ml, 0.825 mmoles) were added and the reaction was allowed to come to room temperature. After approximately 25 minutes, additional triethylamine (0.25 ml, 0.179 mmoles) was added. After a total reaction time of 45 minutes, the reaction solution was applied to a 2.5×100 column of LH-20 in methanol and fractions (approximately 7 ml) collected. Fraction 22-28 contained 0.16 g of the desired product.

EXAMPLE 5

Preparation of MeOSuc-Ala-Ala-Pro-boroPro-pinacol.

MeOSuc-Ala-Ala-Pro-OH was prepared by the procedure described in Kettner et al., *J. Biol. Chem.*, 259: 15106–15114 (1984). MeOSuc-Ala-Ala-Pro-OH (1.59 g. 4.28 mmoles) was coupled to H-boroPro-pinacol.HCl (1.00 g, 4.28 mmoles) by the mixed anhydride procedure described for the preparation of Boc-Ala-Pro-boroPro-pinacol except that, after filtration and evaporation of the reaction solvent, it was applied to a 2 cm column containing 10 g of silica gel equilibrated with chloroform. The column was eluted with chloroform and fractions containing the desired product were evaporated and triturated with hexane to yield 0.58 g of a white solid.

EXAMPLE 6

Preparation of Boc-Pro-Thr(OBzl)-boroPro-pinacol.

Boc-Pro-Thr(OBzl)-OH was prepared by coupling Boc-Pro-OSu (the N-hydroxysuccinamide ester of Boc-Pro-OH) to H-Thr (OBzl) - OH. H-Thr (OBzl)-OH.HCL was dissolved in 25 ml of water, $NaHCO_3$ (6.21 g, 73.9 mmoles) and a solution of Boc-Pro-Osu (5.07 g, 16.25 mmoles) in 25 ml of dioxane were added. After stirring 3 hours, the reaction mixture was acidified with hydrochloric acid and the product extracted into ethyl acetate. It was washed with 0.2N HCl prepared in saturated aqueous NaCl, saturated NaCl and dried over anhydrous $Na_2SO_4$. Solvent was evaporated to yield 6.24 g (mp 120°–12.5°).

Boc-Pro-Thr(OBzl)-boroPro-pinacol was prepared by coupling Boc-Pro-Thr(OBzl)-OH (2.70 g, 6.42 mmoles) to H-boroPro-pinacol.HCL(1.50 g, 6.42 mmoles) using the procedure described for Boc-Ala-Pro-boroPro-pinacol. The product (2.4 g) was purified by chromatography on a 2.5×50 cm column of LH-20 in methanol and was obtained as 0.84 g of oil.

EXAMPLE 7

Preparation of Boc-Pro-Thr-boroPro-Pinacol

Boc-Pro-Thr-boroPro-pinacol was prepared by hydrogenation of Boc-Pro-Thr(OBzl)-boroPro-pinacol (from Example 6, 0.585 g, 0.79 mmoles). The protected peptide was dissolved in 100 ml of methanol and was hydrogenated for 2 hours on a Parr apparatus in the presence of 0.5 g of 10% Pd/C. The reaction was filtered and solvent evaporated. The product was allowed to stir with hexane, and hexane insoluble material removed by filtration. The filtrate was evaporated to yield the desired product (0.24 g) as a white foam.

USE

The compounds of formula 1 above can be administered in an effective amount either alone or in combination with a pharmaceutically acceptable carrier or diluent.

The compounds of formula 1 or compositions thereof can be used to treat mammals, e.g., humans, suffering from or subject to infections by pathogenic bacteria which produce deleterious post prolyl cleaving enzymes, e.g., the IgA1 protease of *Haemophilus influenza*. The compounds or compositions can be administered alone or in combination with one another, or in combination with other therapeutic agents. The dosage level may be 1–500 mg/kg/day of the formula 1 compounds.

When administered to mammals (e.g., orally, topically, intramuscularly, intraperitoneally, intravenously, parenterally, nasally or by suppository), the compounds of the invention enhance the ability of e.g., the immune system of the mammal to fight bacteria which produce an IgA-1 protease, thus slowing the course of infection by the bacteria.

Other embodiments are within the following claims.

We claim:

1. A compound, having the structure

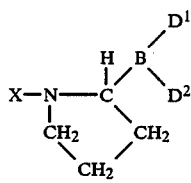

where each $D^1$ and $D^2$, independently, is a hydroxyl group or a group which is capable of being hydrolysed to a hydroxyl group in aqueous solution at physiological pH;

and X comprises an amino acid or a peptide which mimics the site of a substrate recognized by a post prolyl cleaving enzyme.

2. The compound of claim 1 wherein X comprises a blocking group.

3. The compound of claim 2 wherein X comprises an acetyl group.

4. The compound of claim 1 where X is pro-, thr-pro-, ala-pro-, ala-ala-pro-, ser-thr-pro-, pro-ser-, pro-thr- or ser-pro-.

5. The compound of claim 1, said enzyme being a postprolyl cleaving enzyme.

6. The compound of claim 5, said enzyme being a serine protease.

7. The compound of claim 5, said enzyme being an IgA1 protease.

8. The compound of claim 1, wherein said compound has a binding constant to said enzyme of at least $10^{-10}$M.

9. The compound of claim 6, wherein said compound has a binding constant of at least $10^{-7}$M.

10. The compound of claim 1 admixed within a pharmaceutically acceptable carrier substance.

11. A compound having the formula

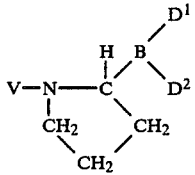

where V is $(CH_3)_3$Si— or H—, and each $D^1$, $D^2$ independently is a group which is capable of being hydrolyzed to a hydroxyl group in aqueous solution at physiological pH.

12. The compound of claim 1 or 11 wherein, each $D^1$ and $D^2$ is, independently, F or $D^1$ and $D^2$ together are a ring containing 1 to about 20 carbon atoms, and optionally heteroatoms which can be N, S, or O.

* * * * *

UNITED STATES PATENT AND TRADEMARK OFFICE
CERTIFICATE OF CORRECTION

PATENT NO. : 4,935,493
DATED : June 19, 1990
INVENTOR(S) : Bachovchin et al.

It is certified that error appears in the above-identified patent and that said Letters Patent is hereby corrected as shown below:

Column 1, line 5: Please insert --This invention was made with government support under DE07257 and GM27927 awarded by the National Institutes of Health. The government has certain rights in the invention.--

Signed and Sealed this

Seventeenth Day of April, 2001

*Attest:*

NICHOLAS P. GODICI

*Attesting Officer*  *Acting Director of the United States Patent and Trademark Office*